United States Patent [19]
McCloskey et al.

[11] Patent Number: 6,128,079
[45] Date of Patent: Oct. 3, 2000

[54] FIBER OPTIC PROBE AND SYSTEM FOR MEASUREMENT OF MOISTURE IN STEAM TURBINES

[75] Inventors: Thomas H. McCloskey, San Jose, Calif.; Stephen Hesler, Rochester, N.Y.; Alexander Liberson, Rochester, N.Y.; Russell H. Maurer, Rochester, N.Y.

[73] Assignee: Electric Power Research Institute, Inc., Palo Alto, Calif.

[21] Appl. No.: 09/276,011

[22] Filed: Mar. 25, 1999

[51] Int. Cl.⁷ .................................................. G01N 21/49
[52] U.S. Cl. .......................... 356/338; 356/328; 356/342
[58] Field of Search .................................... 356/319, 326, 356/328, 338, 342, 432, 436, 440, 441, 442; 250/573, 574, 576

[56] References Cited

U.S. PATENT DOCUMENTS

| | | | |
|---|---|---|---|
| 4,497,577 | 2/1985 | Sato et al. | 356/336 |
| 5,139,334 | 8/1992 | Clarke | 356/301 |
| 5,303,036 | 4/1994 | McLachlan et al. | 356/440 |

FOREIGN PATENT DOCUMENTS 2281967  3/1995  United Kingdom .

*Primary Examiner*—F. L. Evans
*Attorney, Agent, or Firm*—Flehr, Hohbach, Test, Albritton & Herbert

[57] ABSTRACT

There is described a fiber optic probe and associated system for measuring light extinction due to forward scattering by steam droplets. A system is also described for analyzing the light transmissibility to produce a measure of steam wetness.

5 Claims, 2 Drawing Sheets

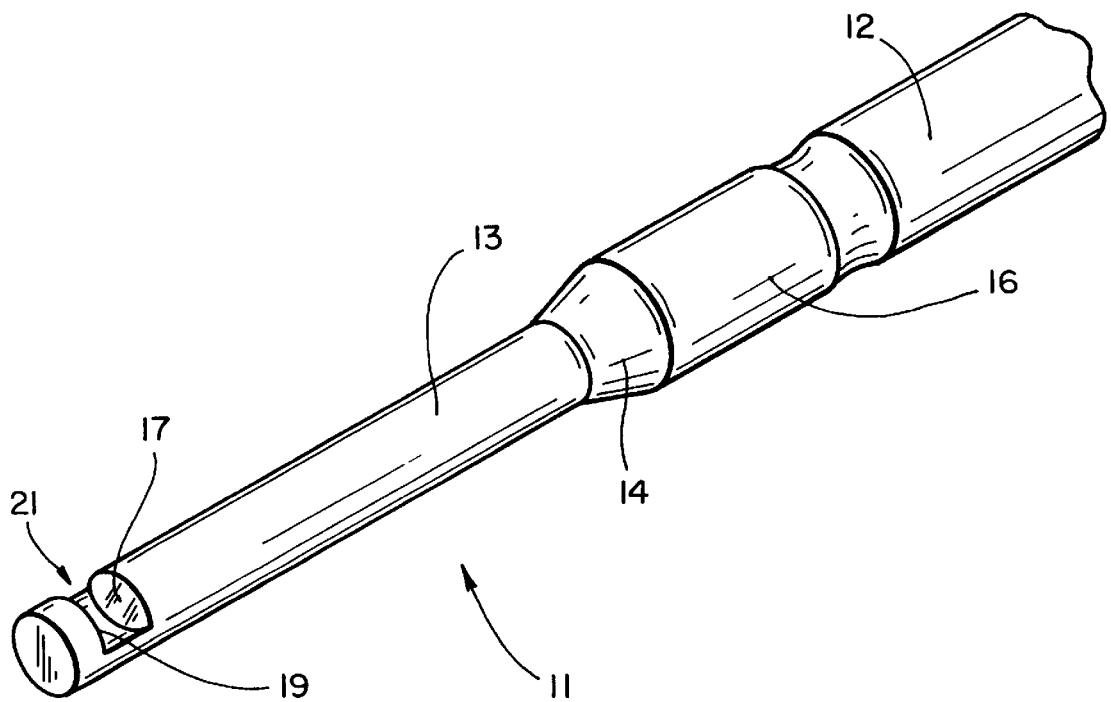
FIG_1
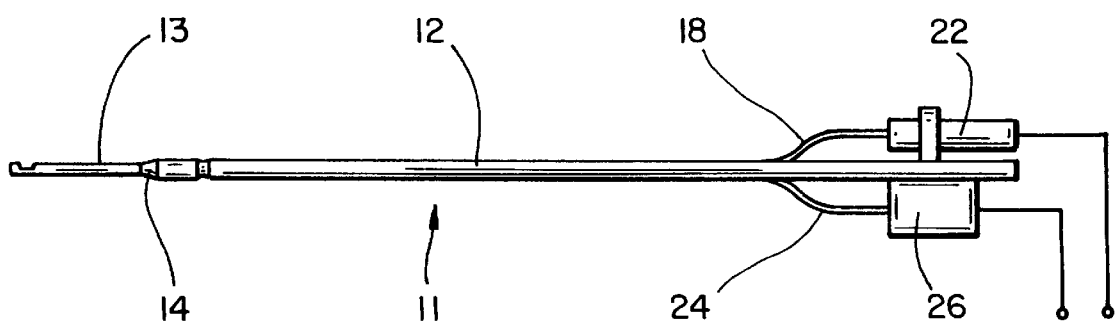
FIG_2

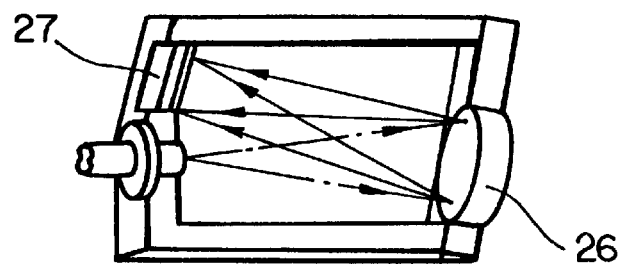
FIG_3
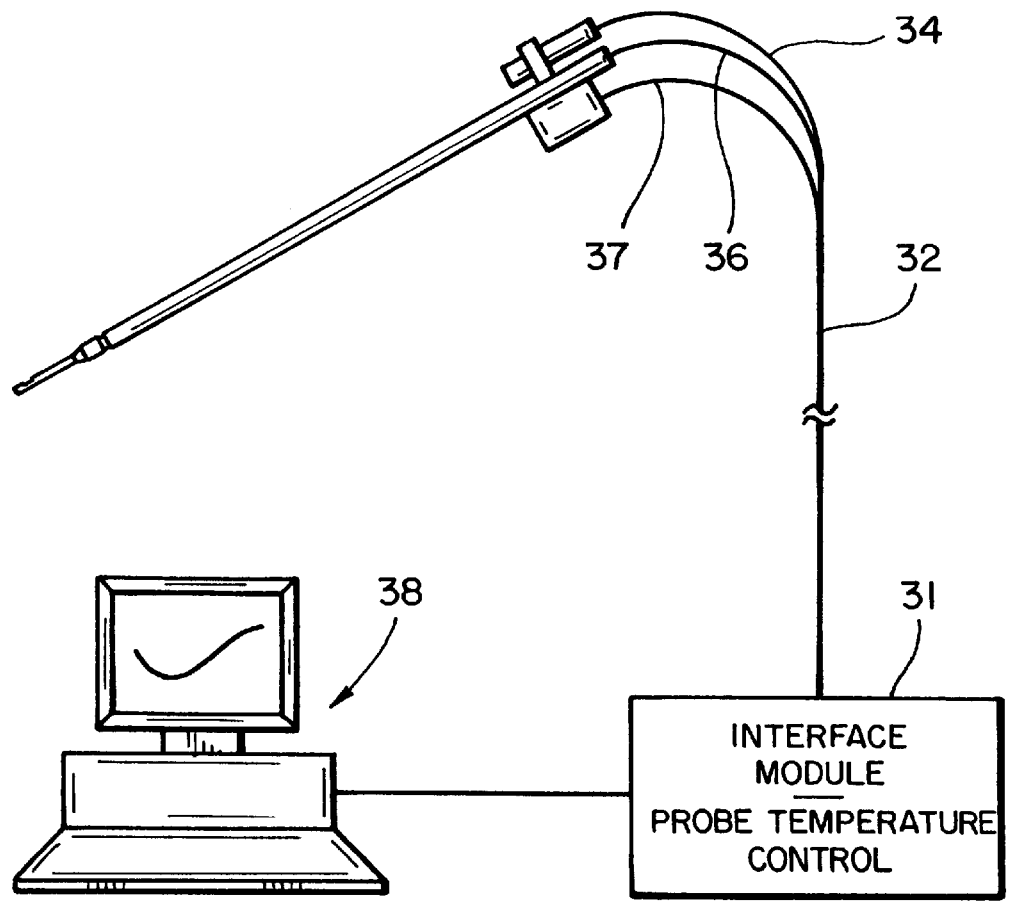
FIG_4

FIBER OPTIC PROBE AND SYSTEM FOR MEASUREMENT OF MOISTURE IN STEAM TURBINES

BRIEF DESCRIPTION OF THE INVENTION

This invention relates to a fiber optic probe and system for measuring steam moisture or quality in steam turbines.

BACKGROUND OF THE INVENTION

Steam quality at various locations in a steam turbine is an important parameter since it plays a large role in the turbine's mechanical performance. Steam quality can also be used for diagnostic purposes and malfunction detection.

Historically, calorimeters have been used to determine steam quality. Difficulties with obtaining proper isokinetic steam samples limited the practical use of this approach. Beginning in the early 1980s, the British CEGB developed an optical traversing probe which relied on the forward light-scattering characteristics of sub-micron sized water droplets to characterize both the size distribution and the concentration of these drops. Analysis techniques were developed to convert the optical data to the wetness fraction and enthalpy. The CEGB data reduction method was based on the Mie scattering theory, and the mathematics involved inversion of ill-conditioned matrices to deduce size distributions. Comparison of results from several LP traverse tests performed in parallel with heat rate tests by the CEGB were reportedly very good, with differences in LP cylinder efficiency on average less than one percent. During the past fifteen years, researchers in both Europe and Japan have published descriptions of various similar optical techniques for measurement of steam wetness based on light-scattering characteristics of the condensed aerosol.

U.S. Pat. No. 4,137,462 describes a probe for measuring steam quality. The light from a monochromatic light source is transmitted to a measuring zone by a fiber optic bundle. The light passes through the measuring zone and is reflected back to a photodetector. The photodetector measures the intensity of the light. The ratio of the light intensity to the light intensity for dry steam is a measure of moisture content.

U.S. Pat. No. 4,497,577 describes a steam wetness measuring apparatus which comprises a light source, a part defining a measuring space when the apparatus is inserted into a wet steam flow, an optical fiber bundle for transmitting the incident light beam from the light source to the measuring space, and optical fiber bundles for transmitting to a photoelectric converter element a plurality of scattered light beams of different scattering angles obtained by radiating an incident light beam on the measuring space.

The prior art wetness probes do not provide a forward light scattering design which employs light having a wide wavelength range, and do not measure scattered light intensity for different wavelengths.

SUMMARY OF THE INVENTION

In accordance with the present invention there is provided an improved fiber optic probe for measuring light extinction due to forward scattering over a broad wavelength range. The spectral transmissivity is analyzed to produce droplet size distribution and liquid volume based on Mie scattering theory.

A fiber optic probe in accordance with the present invention includes a source of light having a broad wavelength range; a probe tip having a scattering volume defined by a collimating lens and a reflector; a fiber optic cable for delivering light from said source of light to said collimating lenses whereby the collimated light travels through said volume and is reflected back through the volume to said collimating lens; a fiber optic cable for transmitting the reflected light to a diffraction grating which forms a plurality of spectral lines or bands over said broad wavelength range; and a photodiode array for receiving said spectral lines and providing an electrical output signal representative of the intensity of the light at each of said spectral lines or bands.

The wetness fraction in condensing steam is assessed by measuring the percentage reduction in light intensity ($I/I_0$) as a function of wavelength $\lambda$. This ratio is referred to as transmission and is formed by two separate measurements. The measurement of spectral intensity with no scattering ($I_0$) is a reference measurement, and is obtained by placing the probe tip in dry steam or air flow and obtaining the intensity at each wavelength. Light intensity measurements at each wavelength are then obtained and divided by the stored reference intensity for each wavelength to produce a spectral transmission plot, $I/I_0$. Offset voltage of the photodiode array is removed by subtracting the signal produced under zero light conditions.

BRIEF DESCRIPTION OF THE DRAWINGS

The invention will be more clearly understood from the following detailed description of a preferred embodiment when read in conjunction with the accompanying drawings in which:

FIG. 1 is a perspective view of a fiber optic probe in accordance with one embodiment of the present invention;

FIG. 2 schematically shows the optical elements of a probe in accordance with the present invention; and FIG. 3 shows the diffraction grating and photodiode array for obtaining wavelength scattering data.

FIG. 4 shows the fiber optic probe and the associated system for measurement of moisture in steam turbines.

DESCRIPTION OF PREFERRED EMBODIMENT

The moisture measurement system of the present invention includes a fiber optic probe 11, FIGS. 1 and 2, which is inserted into the steam turbine to measure the quality of the steam at various locations. The probe includes means for applying light having a broadband of wavelengths to a sensing volume. The light of various wavelengths is scattered differently by the spheroidal water droplets in two-phase steam flow, depending on the ratio of droplet diameter to wavelength of incident light. Forward scattered light is light that is aligned with the direction of incident light. However, in general, light is scattered in all directions as defined precisely by Mie scattering theory, derived from Maxwell's equations. These characteristic scattered light intensity patterns are measured by the probe in the form of an optical transmission efficiency, or simply put, the ratio of light intensity transmitted through a medium containing droplets in suspension I to the intensity of light transmitted with no droplets present, $I_0$. This spectral transmission ratio is always less than or equal to one, and is mainly dependent on the light wavelength to droplet diameter ratio (referred to as droplet size parameter). Since the light scattering is precisely defined based on Mie theory for known size parameters and relative refractive indices, measurement in two-phase steam flow becomes a process of: (a) measuring spectral transmission efficiencies, and (b) employing Mie theory to deduce the droplet size distribution from the measured light transmission data.

The probe 11 includes a probe tube 12 and replaceable probe body tips 13 held by collar 14 connected to adapter 16. The probe body includes a collimating lens 17 which cooperates with the end of fiber bundle 18, FIG. 2. A reflector 19 is spaced from the lens. The distance between the collimating lens and reflector defines the measuring or scattering volume 21. Probe bodies can be selected to provide the desired scattering length. Scattering lengths between 20 mm and 40 mm have produced good optical signals. The probe tube 12 extends through access ports in the steam turbine so that the scattering volume can be placed at various locations in the turbine for determining steam quality as will be presently described.

Referring to FIG. 2, the probe includes a pulsed light source 22. By way of example, the light source 22 provides visible and ultraviolet light in the range of 230 to 930 nanometers to the fiber optic bundle 18. The light emitted from the end of the fiber bundle 18 is collimated by the lens 17, travels through the measurement volume 21, is reflected or folded back through the measurement volume, and focused by the lens into the end of fiber bundle 24. The light emitted from the end of fiber optic bundle 24 is diffracted by the diffraction grating 26, FIG. 3, to form a number of spectral lines of discrete wavelengths which impinge upon the photodiode array 27. The photodiode array 27 is positioned to measure the intensity at each band of the scattered light. For example, the diffraction grating splits the received light into +1024 discrete wavelengths. The electrical output from the photodiode array for each discrete wavelength is the intensity of the light at that wavelength after it has passed through the volume 21 reflected by reflector 19 and focused into the end of fiber bundle 24. The reflector 19 and lens 17 are heated internal to the probe, not shown, to prevent condensation. The fiber bundles 18 and 24, which transmit and receive light, are positioned adjacent to each other at the focal point of the lens 17, resulting in a compact probe. All of the critical components of the probe are "on-board" the probe, thereby eliminating the need for flexible fiber optic cable connections to the light source and the diffraction grating. The associated processing and control equipment is connected to the probe by electrical wires.

Referring to FIG. 4, the probe assembly is connected to an interface module 31 via electrical cable 32. The cable includes a lead 34 for controlling the pulsed light source 22, a lead 36 for applying heater power, and a lead 37 for applying power to the diode array and transmitting the diode array output to the interface module 31. The interface module includes power supplies, light source shutter controls and probe heater temperature control. Operation of the interface module is controlled by a customized user interface resident on a computer workstation 38. Dry flow reference data is obtained and stored and is divided into all subsequent measurements of scattered light to derive the percent reduction in light intensity caused by scattering (transmission data).

The photodiode array has inherently high frequency response. As a result, fluctuations in scattered light intensity can be detected. It is typical to average out these fluctuations by integrating the scattered light intensity over time. The inherently nonsteady nature of wet steam flow requires averaging of the spectral data to yield accurate and repeatable light transmission data. The speed of the spectrophotometer when coupled with the computer workstation produces integration times on the order of seconds. Multiple averages are taken to ensure repeatable results at each point, and a set of three averages typically requires a scanning time of less than three minutes.

The workstation which controls the spectrophotometer (diffraction grating and photodiode array) also acts as a data storage device. The multitasking capability of the computer also permits processing of the test data in near real time.

The following summarizes the method followed by the programmed computer for processing the intensity data. The fundamental equation governing light extinction due to scattering is Bouger's Law and can be written for monodisperse (single drop size) aerosol suspensions at a single light wavelength $\lambda$ as:

$$I/I_0 = e \quad (1)$$

where:

I is measured light intensity $I_0$ is reference light intensity with no scattering n is droplet concentration A is droplet cross-sectional area $(\pi D^2/4)$ E is Mie extinction coefficient, a function of $(D/\lambda)$, where $\lambda$ is the wavelength of light; Mie scattering data is derived as a function of the relative index of refractions between liquid and vapor phase t is scattering length (2× slot length of probe tip for folded light path)

Equation (1) can be rewritten as:

$$g = 1/t \cdot \ln(I_0/I) = n \cdot A \cdot E \quad (2)$$

where:

g is defined as turbidity

For real drop size distributions which exhibit polydispersity (multiple drop sizes) or bimodality (multiple distributions), equation (2) must be expressed in integral form for a specific wavelength $\lambda$ as:

$$g(\lambda) = 1/t \cdot \ln[I_0(\lambda)/I(\lambda)] = \int_0^\infty [\pi/4 \cdot n \cdot D^2 \cdot E] f(D) dD \quad (3)$$

where:

$\lambda$ is light wavelength f(D) is droplet size distribution

Fore typical light transmission data, the data reduction program converges on a droplet size distribution f(D) based on the following:

A. a cubic spline representation of the distribution f(D)

B. addition of an exponentially damped "tail" section of the distribution; within this tail section f(D)→0 as D→∞.

C. the cubic spline is linked to the exponential tail section such that slope continuity is maintained at the interface D. maximizing the smoothness of the cubic spline, as defined by minimizing the integral rate of curvature across the range of wavelengths The numbness scheme typically iterates, trying 100–200 different droplet size distributions, f(D). An optimization scheme is used to converge on the combination of distribution function and tail section which produces the best fit against the measured turbidity plot. The final difference between the converged solution and the measured turbidity is less than one percent, on a least-squared basis. The strength of this method of optical data reduction is that a wide range of polydispersed or bimodal drop distributions can be directly evaluated, due to the general nature of the cubic spline and optimization scheme used to characterize the distribution.

The next step is to evaluate the total liquid mass flow from the derived size distribution f(D):

$$L = \pi/6 \cdot v_1 \int_0^\infty f(D)(D^3)d(D) = \pi/6 \cdot v_1 \cdot M_3 \quad (4)$$

where:

L is the total liquid mass flow
$v_1$ is the specific volume of the liquid phase
$M_3$ is the third moment of droplet size distribution Finally:

$$W = L/(L + 1/V_v) = 1/(1+\omega) \quad (5)$$

where:

W is wetness fraction
$V_v$ is the specific volume of the vapor phase, at the local static pressure
$\omega$ replaces the expression $6 \cdot v_1/\pi \cdot V_v \cdot M_3$.

Thus there has been provided an improved optical probe for measuring scattered light intensity of light which passes through steam at a plurality of wavelengths over a broad light frequency band. There is also described a system for processing the intensity information to provide a measure of the steam wetness.

The foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A fiber optic probe system comprising:

a fiber optic probe for measuring steam quality, a source of light having a broad wavelength range, a probe tip having a scattering volume defined by a collimating lens and a reflector, a first fiber optic cable for delivering light from said source of light to said collimating lens whereby collimated light travels through said volume and is reflected back to said collimating lens, a second fiber optic cable for receiving the reflected light focused by said collimating lens, a diffraction grating for receiving reflected light from said second fiber optic cable and breaking it into a plurality of spectral lines, a photodiode array for receiving said spectral lines and providing an electrical output signal representative of the intensity of the light at each of said spectral lines, a computer, and an interface module for applying control signals from said computer to said source of light and for applying the output signals from said photodiode array to said computer.

2. A fiber optic probe system as in claim 1 in which said source of light and said diffraction grating and photodiode array are mounted on said probe.

3. A fiber optic probe system as in claim 1 in which said probe includes heater means for heating said collimating lens and reflector.

4. A fiber optic probe system as in claim 1 in which said computer is configured to process said output signal and provide an output representing the quality of the steam.

5. A fiber optic probe system as in claim 4 in which the steam quality is steam wetness.

* * * * *